United States Patent [19]

Comparetto

[11] Patent Number: 4,664,102

[45] Date of Patent: May 12, 1987

[54] ELECTRONIC GUIDANCE FOR BONE WEDGE EXCISION

[76] Inventor: John E. Comparetto, 322 Freeman Ave., Audubon, Iowa 50025

[21] Appl. No.: 749,475

[22] Filed: Jun. 27, 1985

Related U.S. Application Data

[63] Continuation-in-part of Ser. No. 721,640, Apr. 10, 1985, and a continuation-in-part of Ser. No. 534,505, Sep. 21, 1983, abandoned.

[51] Int. Cl.⁴ ............................................. A61F 5/04
[52] U.S. Cl. ............................................... 128/92 VY
[58] Field of Search ....... 128/92 XY, 92 XX, 92 XW, 128/92 X

[56] References Cited

U.S. PATENT DOCUMENTS

| 4,433,681 | 2/1984 | Comparetto | 128/92 VY |
| 4,501,268 | 2/1985 | Comparetto | 128/92 VY |
| 4,502,474 | 3/1985 | Comparetto | 128/92 VY |

Primary Examiner—Gene Mancene
Assistant Examiner—C. W. Shedd

[57] ABSTRACT

An electronic guidance means is utilized in conjunction with a set of guide arms, to accurately measure and display angular changes to make correction in bone surgery.

7 Claims, 9 Drawing Figures

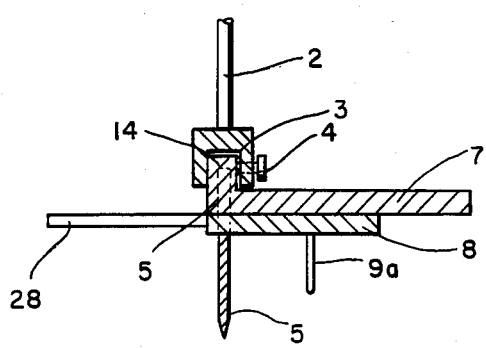
FIG. 4.
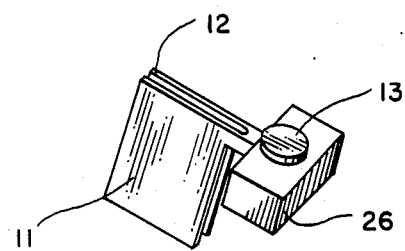
FIG. 6.
FIG. 5.
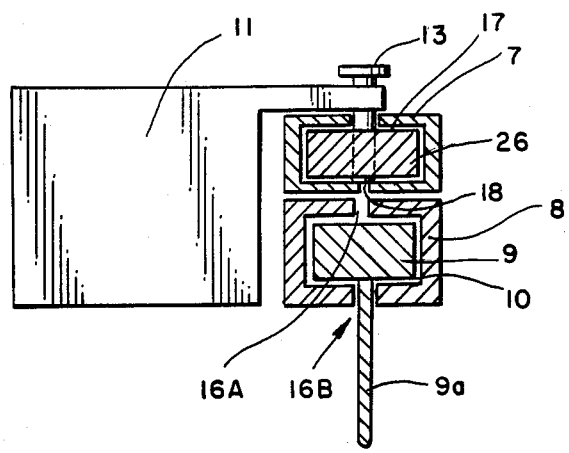

ELECTRONIC GUIDANCE FOR BONE WEDGE EXCISION

DESCRIPTION OF THE INVENTION

This invention is a continuation-in-part of Ser. No. 721,640, filed on Apr. 10, 1985 and Ser. No. 534,505, filed on Sept. 21, 1983 now abandoned.

BACKGROUND OF THE INVENTION

1. Field of the Invention

In bone surgery it is often required that a wedge of bone be taken to make a correction of deformity. This has been traditionally done by making "pie shaped" wedges and more recently by the "curved-v", more properly called the arcuate wedge, osteotomy that makes precise wedges and therefore precise corrections.

2. Prior Art

The making of arcuate wedge cuts in bone has been described in U.S Pat. Nos. 4,150,675, 4,349,058, 4,501,268, and 4,502,474, by this inventor. It is further described in patent application Ser. Nos. 534,505 and 721,640. Various guides are used to make a precise wedge from an arcuate osteotomy of bone. In addition guides have been made adjustable to allow the surgeon to take a desired arcuate wedge segment in one osteotomy while being able to change the angular dimension of the guide while in surgery for the next osteotomy to be performed. These guides have been fabricated in prototype with deep slots that converge toward each other (U.S. Pat. No. 4,501,268) so that the surgeon can take a precise "pie shaped" wedge if he requires to; this is seldom since there is an iatrogenic shortening of bone with this type of wedge.

OBJECTS OF THE INVENTION

An object of the invention is to provide an electonic apparatus that can encode mechanical angular displacement in the taking of bone wedges.

Another object of the invention is to provide an electronic screen to display angular displacement in the taking of precise bone wedges.

A further object of the invention is to provide a bone pin means that will allow the rotation of the electonic encoding apparatus on said bone pin.

A still further object of the invention is to provide a receptacle means at an end of the electronic encoding apparatus shaft means that will rotate freely on a bone pin.

Another object of the invention is to provide a slot means in a first guide arm means.

Another object of the invention is to provide a movable pin means for said slot means.

A further object of the invention is to provide a slot means in a second arm means.

A still further object of the invention is to provide a third slot means to slide adjustably in said second arm's slot means.

Another object of the invention is to provide a fixation means that allows for the movement of the second arm in unison with the shaft of the electronic encoder means.

BRIEF DESCRIPTION OF DRAWINGS

FIG. 4 is a cross sectional view through the receptacle means, guide arm means and the bone pin.

FIG. 5 is a cross sectional view through guide arms at zero degrees showing the third adjustable guide arm means.

FIG. 6 is a perspective view of the adjustable third guide arm means.

DETAILED DESCRIPTION OF THE INVENTION

In U.S. Pat. No. 4,504,474 (Mar. 5, 1985, Comparetto), a microcomputer used in conjunction with a potentiometer (rheostat) device was described in the patent specifications. A change in resistance load corresponded to a rotational change of a central member, which was caused by the angular displacement of a bone guide means.

In this instant invention an electromechanical apparatus consisting of the above mentioned potentiometer or a preferred embodiment of the invention comprising an optical encoder is described each having essential guidance arms to both register angular change as well as provide means for the taking of the arcuate wedge and the curved ellipsoidal wedge of bone (more commonly known as the "pie-shaped" wedge). The curved ellipsoidal wedge should be seldom used since it iatrogenically causes bone shortening; presumably this would be the only justifiable reason for its use, i.e. a desired shortening of a specific bone.

The optical encoder utilizes phototransistors and the interaction of grid networks that measure incremental pulsations that is outputted as angular change on a display screen such as a semiconductor diode, cathode ray tube or liquid crystal screen. The following descriptions of the invention refers particularly to this preferred form of the invention, but also essentially describes the method and apparatus utilizing a variable resistance and a microcomputer to measure angular change.

Figure 1:
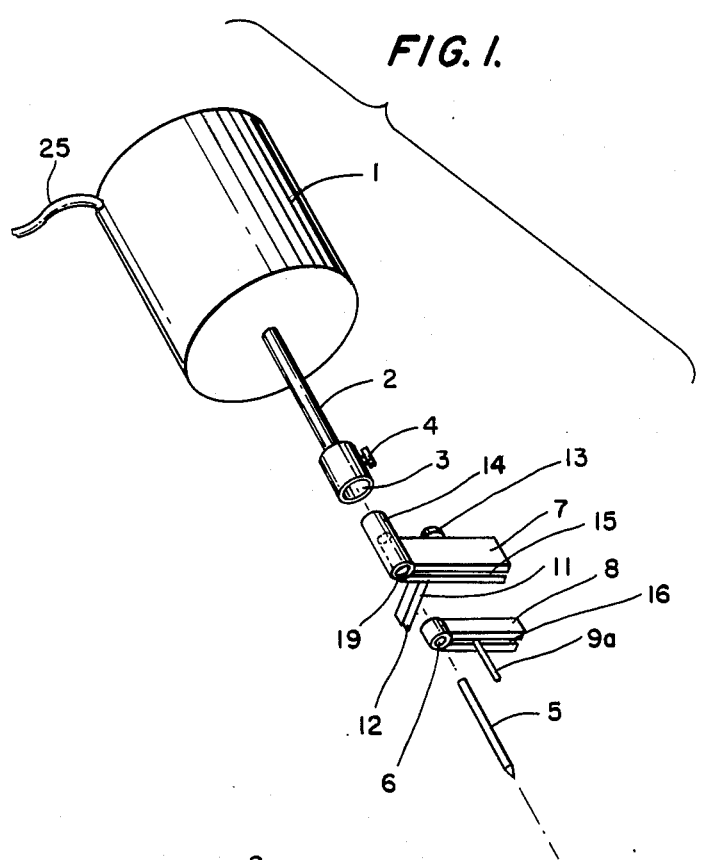
FIG. 1 is a perspective view of an electronic guidance apparatus for bone wedge taking.
Figure 2:
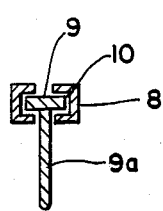
FIG. 2 is a cross sectional view of a first guide arm means including the movable guide pin.
Figure 3:
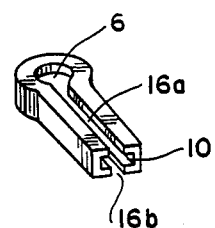
FIG. 3 is a perspective view of the guide arm means of FIG. 1 without the guide pin.
Figure 7:
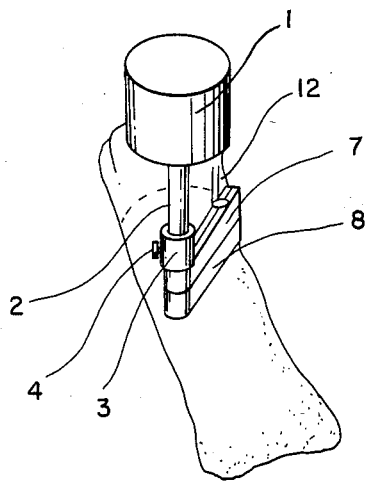
FIG. 7 is a perspective view of the electromechanical apparatus taking an arcuate wedge of bone.
Figure 8:
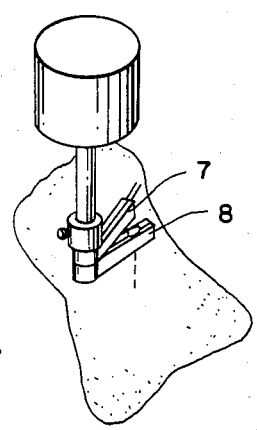
FIG. 8 is a perspective view of the electromechanical apparatus taking an curved ellipsoidal ("pie-shaped") wedge of bone.
Figure 9:
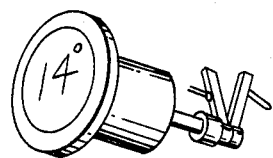
FIG. 9 is a perspective view of a display screen means at the end of an encoding apparatus.

In FIG. 1, cylinder (1) contains an optical encoder or a potentiometer device linked by cable (25) to a power source. Shaft (2) rotates in response to the angular change of guide arm (7) which is rigidly affixed to shaft (2) either permanently or by means of receptacle (3) and set screw (4) which receives guide arm extension (14) seen in FIGS. 1 and 4. Guide arm (7) has a pivotal end directly below and in the center of the extension (14). In this pivotal end there is a recess (19) into which the end of a bone pin (5), as is seen in FIGS. 1 and 4, fits smoothly with no play or wobble. The guide arm (7) can smoothly rotate on this bone pin. The bone pin (5) is the rotational center of an arcuate cut as made with a bone cutter as decribed in U.S. patent application Ser. No. 721,640, or is the apex of a conventional curved ellipsoidal wedge. In guide arm (7) is a longitudinal slot means (15) that can be described as key hole shaped in cross section. It can have a rounded cross sectional upper portion or any other convenient shape to receive a body member (26), depicted as rectangular in cross section in FIG. 6, of a movable guide that can be used to make straight angular cuts from an arcuate cut when said straight cuts are desired to be at an acute angle to the respective tangents of the arcuate cut. When a perpendicular to the tangent of the arcuate cut straight cut is desired then guide arm (7) is used without the movable slot arm. In FIG. 5 the body member (26) is a rectangular oblong to fit into the upper rectangular slot (17) of the key hole configuration. At the uppermost extent of this body member is a contiguous member (21) that continues as two flutes (11) that form slot means (12). Set screw (13), seen in FIGS. 5 and 6 can affix the slot means (12) at any desired position along slot means (15), which would be determined by its intersection with a previously made arcuate cut. Set screw (13) is wider than the narrower longitudinal member (18) and engages the rectangular portion at the point immediately above the opening to channel (18). If the surgeon desired to take an acruate wedge off an arcuate cut that was perpendicular to the respective tangents to the arcuate cut or if he wished to take a curved ellipsoidal wedge, the slot member (12) would be removed from the longitudinal slot (15) of the guide arm (7) so that the straight cutting blade could pass through both upper portion (17) and lower portion (18) to make the straight cuts. Guide arm (8) seen in FIGS. 2, 3, 4, and 5, has a round hole (6) at one end that can pass over a bone pin (5), smoothly fitting and rotating on said bone pin without play or wobble. In a preferred embodiment of the invention guide arm (8) is shorter in length than guide arm (7) so that the first straight cut in the taking of an arcuate cut is more readily accomplished. In guide arm (8) there is a longitudinal channel having openings (16a) and (16b) which are the same width as section (18) of guide arm (7). Immediately above and below openings (16b) and (16a) respectively, there is a wider channel member (10) through which movable pin member (9a) smoothly articulates and moves through said channel by means of head portion (9). Guide arm (8) is positioned on the bone pin (5), so that it lies directly on the bone and the pin member (9a) is within the arcuate cut at its most internal extent, that is the internal end of the arcuate cut into the bone. In the case of the curved ellipsoidal cut the pin (9a) is positioned anywhere within a first straight cut that end at the point where bone pin (5) enters the bone. At the time the movable pin (9a) is positioned in these cuts as described above, the guidance arm (7) is positioned directly over guide arm (8) as depicted in FIG. 5. The optical encoder is zeroed at this point, and the first straight cut is made. Guide arm (7) is now rotated on the bone pin (5) thereby simultaneously rotating the shaft of the encoder. The output of this angular change is displayed on an display screen and the angular displacement of guide arm (7) from the zero positioned guide arm (8) is stopped by the surgeon at the desired amount. The second straight cut can now be made yielding the wedge. In FIG. 7 is seen a depiction of the invention at the zero position in taking an acute angled arcuate wedge. In FIG. 8 is seen a depiction of guide arm (7) being positioned to take a second straight cut in the formation of a curved ellipsoidal ("pie-shaped", or sector shaped) wedge. In FIG. 9 is seen a perspective view of a display screen affixed to the end of electronic bone wedge guide apparatus. The display screen could be remotely placed such as in a convenient place on the operatory wall.

From the foregoing description, one skilled in the art can easily ascertain the essential characteristics of this invention and without departing from the spirit and scope therof, can make various changes and modifications of the invention to adopt to its various uses.

What is claimed is:

1. The electronic bone wedge guide comprising an electronic optical encoder means, having a shaft means further comprising a receptacle means that receives an extension means of a guide arm means and further comprising a fixation screw means to securely and rigidly fasten said guide arm extension means to the shaft so that the guide arm means may cooperatively and simultaneously rotate with the shaft means to record angular displacement of said guide arm means from a zero position by the comparative change of encoder grids caused by the rotation of said shaft and the pulses thus generated being digitalized and sent to a display screen and display screen indicating the angular changes.

2. The guide arm means of claim 1 further comprising a longitudinal slot means having a wide internal cross sectional dimension to engage a body of a movable slot member at any point along the longitudinal slot means, said guide arm means having a hole at one end that fits over a bone pin and smoothly rotates on said bone pin, said guide arm means further comprising a lower narrower longitudinal channel that communicates with the upper wider channel through its entire length, said narrower channel capable of admitting a straight cutting saw blade.

3. The movable slot member of claim 2 that comprises a body means that closely conforms in cross section to the widest section of the internal longitudinal channel of the guide arm, said movable slot further comprising two flute means that form said movable slot and a set screw in said body means that passes through the body means to engage the longitudinal channel at a desired position, said engagement occuring at a point above the lower channel means.

4. The guide arm means of claim 1 comprising a longitudinal slot means open at top and bottom, further comprising a wider internal dimension having a shape that conforms with the cross section of the head of a movable pin means, said movable pin means capable of traveling to any position along the longitudinal channel, said top and bottom openings of said longitudinal channel capable of admitting a straight cutting saw blade.

5. The electronic device of claim 1 wherein the cylinder and shaft comprises a potentiometer, said shaft rotating with a rigidly attached guide arm, said rotations causing a measurable change in resistance, said change being analyzed by a microcomputer to yield an angular digitalized readout on a display screen.

6. The process of taking wedges of bone by first zeroing an optical encoder and taking a first cut into bone, by then rotating a guide arm means to a second position angularly displaced from the first cut position, said first cut position being maintained by a reference pin extending from a second guide arm into the first cut in bone, said rotated guide arm means rotating on a bone pin which is the center of an arcuate cut or the apex of a sector shaped cut, said rotation of the guide arm simultaneously rotating the rigidly affixed shaft member of an optical encoder, said rotation of the shaft means causing impulses in interacting gridworks to send digitalized impulses to a display screen that indicates the desired angular displacement of the guide arm and its saw slot means so that a second straight cut in bone can be made and removing the wedge of bone defined by the first and second cut.

7. In bone surgery, the process of defining the location of a first and second cut in a bone by making a first straight cut in a bone, locating a potentiometer in relation to said first cut, zeroing said potentiometer, said potentiometer having a shaft that is rotated in accordance with the rotation of a slot means in a guide arm means, rotating said shaft, said rotation causing a change in electrical resistance that is analyzed and interpreted by a microcomputer that gives a digital read out of the angular change on a display screen to define the angular location of the second cut.

* * * * *